US009619925B2

(12) United States Patent
Leber et al.

(10) Patent No.: US 9,619,925 B2
(45) Date of Patent: Apr. 11, 2017

(54) METHOD AND IMAGE-PROCESSING SYSTEM FOR GENERATING A VOLUME-VIEWING IMAGE OF THE INTERIOR OF A BODY

(75) Inventors: Carlos Leber, Limburg (DE); Michael Sühling, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 427 days.

(21) Appl. No.: 12/842,185

(22) Filed: Jul. 23, 2010

(65) Prior Publication Data

US 2011/0026795 A1 Feb. 3, 2011

(30) Foreign Application Priority Data

Jul. 31, 2009 (DE) .......................... 10 2009 035 441

(51) Int. Cl.
| | |
|---|---|
| G06K 9/00 | (2006.01) |
| G06T 15/08 | (2011.01) |
| A61B 6/03 | (2006.01) |
| A61B 6/00 | (2006.01) |
| A61B 8/08 | (2006.01) |

(52) U.S. Cl.
CPC .............. *G06T 15/08* (2013.01); *A61B 6/037* (2013.01); *A61B 6/466* (2013.01); *A61B 8/483* (2013.01)

(58) Field of Classification Search
CPC .................................................... A61B 6/037
USPC .......................................... 382/128, 131–133
See application file for complete search history.

(56) References Cited

U.S. PATENT DOCUMENTS

| | | | |
|---|---|---|---|
| 5,187,658 A * | 2/1993 | Cline et al. .................... | 382/128 |
| 2001/0044576 A1 | 11/2001 | Vining | |
| 2004/0015070 A1* | 1/2004 | Liang et al. ................... | 600/407 |
| 2005/0169507 A1* | 8/2005 | Kreeger et al. ............... | 382/128 |
| 2005/0281381 A1 | 12/2005 | Guendel | |

(Continued)

FOREIGN PATENT DOCUMENTS

| | | |
|---|---|---|
| DE | 102004027710 A1 | 1/2006 |
| DE | 202008003517 U1 | 9/2008 |

OTHER PUBLICATIONS

Sokolov, D. "High level methods for scene exploration." J. Of Virtual Reality and Broadcasting, 3.12 (2006): 11, available at http://www.jyrb.org/past-issues/3.2006/1114.*

(Continued)

*Primary Examiner* — Mark Holcomb
(74) *Attorney, Agent, or Firm* — Harness, Dickey & Pierce, P.L.C.

(57) ABSTRACT

A method for generating a volume-viewing image on the basis of three-dimensional image data of the interior of a body generated by way of a medical imaging system is described. In at least one embodiment, a plurality of different functional structures of the body are first of all segmented in the three-dimensional image data. Moreover, structure selection data for fixing functional structures to be visualized is determined. Then, at least one volume-viewing image is generated from the three-dimensional image data on the basis of the segmented functional structures and the structure selection data and the image is output. Moreover, in at least one embodiment, an image-processing system to carry out at least one embodiment of the method is described.

16 Claims, 6 Drawing Sheets

(56) References Cited

U.S. PATENT DOCUMENTS

| | | | | |
|---|---|---|---|---|
| 2006/0269130 | A1* | 11/2006 | Maroy et al. | 382/173 |
| 2007/0127798 | A1* | 6/2007 | Chakraborty et al. | 382/128 |
| 2007/0276225 | A1 | 11/2007 | Chen | |
| 2008/0170769 | A1* | 7/2008 | Assmann | 382/128 |
| 2010/0189317 | A1* | 7/2010 | Lehmann et al. | 382/128 |

OTHER PUBLICATIONS

Bordoloi et al. "View Selection for Volume Rendering".

Dmitry Sokolov, Dimitri Plemenos; "Viewpoint quality and scene understanding", The 6th International Symposium on Virtual Reality, Archaeology and Cultural Heritage VAST (2005) M. Mudge, N. Ryan, R. Scopigno (Editors).

Johanna Beyer et al., "High-Quality Multimodal Volume Rendering for Preoperative Planning on Neurosurgical Interventions", IEEE Transactions on Visualization and Computer Graphics, vol. 13, No. 6, Nov./Dec. 2007, pp. 1696-1703.

S. Seifert et al., "Hierachical Parsing and Semantic Navigation of Full Body CT Data", Proceedings of the SPIE, vol. 7259, pp. 725902-725910 (2009).

Peter Kohlmann, Stefan Bruckner, Armin Kanitsar and M. Eduard Gröller; LiveSync: Deformed Viewing Spheres for Knowledge-Based Navigation; IEEE Transactions on Visualization and Computer Graphics, vol. 13, No. 6, 2007, pp. 1544-1551.

Bordoloi et al. "View Selection for vol. Rendering".

Dmitry Sokolov, Dimitri Plemenos; "Viewpoint quality and scene understanding", The 6th International Symposium on Virtual Reality. Archaeology and Cultural Heritage VAST (2005) M. Mudge, N. Ryan, R. Scopigno (Editors).

Mathias Neugebauer et al.; "Automatische Kamerapositionierung in komplexen medizinischen 3D-Visualislerungen", Inforrnatik aktuell Bildverarbeitung für die Medizin 2007, Verlag Springer Berlin Heidelberg, Teil 12, pp. 318-322 Algorithmen—Systeme—Anwendungen Proceedings des Workshops vom 25.-27. März 2007 in München Alexander Horsch, Thomas M. Deserno, Heinz Handels, Hans-Peter Meinzer and Thomas Tolxdorff; Book; 2007; with English translation.

Johanna Beyer at al., "High-Quality Multimodal Volume Rendering for Preoperative Planning of Neurosurgical Interventions", In: IEEE Transactions on Visualization and Computer Graphics, vol. 13, No. 6, Nov./Dec. 2007, pp. 1696-1703.

\* cited by examiner

METHOD AND IMAGE-PROCESSING SYSTEM FOR GENERATING A VOLUME-VIEWING IMAGE OF THE INTERIOR OF A BODY

PRIORITY STATEMENT

The present application hereby claims priority under 35 U.S.C. §119 on German patent application number DE 10 2009 035 441.7 filed Jul. 31, 2009, the entire contents of which are hereby incorporated herein by reference.

FIELD

At least one embodiment of the invention generally relates to a method for generating a volume-viewing image of the interior of a body on the basis of three-dimensional image data generated by means of a medical imaging system. Furthermore, at least one embodiment of the invention relates to an image-processing system, by which a volume-viewing image can be generated from three-dimensional image data using such a method.

BACKGROUND

Modern medical imaging systems such as magnetic resonance systems, computed tomography systems, PET or SPECT systems, ultrasound installations, etc. are currently able to supply very large amounts of high-resolution image data. A challenge for improving the application of such imaging systems and the results obtained thereby therefore also lies in processing the large amount of measured image data and outputting the latter for a diagnosis and/or intervention planning such that the diagnosing person or planner can identify all relevant information. For this, the three-dimensional image data, which can be measured e.g. in the form of individual slices or else as volume data, is increasingly output in the form of three-dimensional visualizations, referred to as "volume-viewing images" hereinbelow, for example using the so-called "volume-rendering method". Such an output in the form of volume-viewing images simplifies the interpretation for the diagnosing person, particularly when diagnosing vessels and for intervention planning based thereon, because the observer intuitively obtains a spatial awareness of the illustrated structures and does not solely depend on their own spatial sense like in the interpretation of purely two-dimensional slice images.

In clinical routines, such volume-viewing images of a particular structure, e.g. of one or more particular organs, are these days generally displayed in a standard view that is precisely defined in advance and independent of the available data. That is to say one or more volume-viewing images with different viewpoints (the locations of the virtual "camera") are generated by default. The visibility of the structures of interest is controlled, inter alia, by the selection of the so-called "transfer function", which is a measure for how transparent a certain structure is and whether another structure situated therebehind can also be viewed through this structure in the illustration. In addition to transparency, the transfer function can also define the color with which each image voxel in the volume display should be visualized. However, the transfer function is substantially only based on image intensities in this case. This leads to structures with the same image intensity not being displayed independently of one another.

Therefore, in practice, structures determined manually, more particularly organs, are usually freed for a given clinical question in most cases by a specially-trained technical operator. By way of example, this can be brought about with the aid of so-called "punch tools", which punch out a certain region from the image data in a virtual fashion and so a view of structures situated therebehind is made possible. In the process, volume-viewing images are also generated at the same time as so-called "screenshots" from different expedient or information-rich "camera positions". These screenshots are generally sent to a radiologist for diagnosis via a suitable image-data network, for example a picture archive and communication system (PACS). The freeing of organs with the aid of punch tools in particular is relatively time-consuming because the operator often has to load up different viewpoints and must form a suitably-shaped punch tool in each viewpoint such that the view of an organ of interest situated therebehind is cleared, for example by removing organs situated closer to the viewpoint. If it then turns out that the view of the actual target organ of interest is not good enough, the operator has to load up a new viewpoint and there has to again free the region in front of the target organ using a suitably adapted punch tool.

SUMMARY

In at least one embodiment of the present invention, an improved method and an improved image-processing device are developed by which volume-viewing images can be generated from three-dimensional image data of a medical imaging system in a significantly simplified fashion at least semi-automatically, and particularly preferably fully-automatically.

In the method according to at least one embodiment of the invention, a plurality of different functional structures of the body are first of all segmented in the three-dimensional image data as an essential method step. Here, functional structures should be understood to mean e.g. organs, skeleton structures forming functional subunits such as individual ribs or groups of ribs, the entire ribcage, the spine, and also individual bones, vessels, and vessel sections or vessel regions forming functional units, and other tissue structures used to supply certain organs, for example lymph nodes, sections of the lymph system or the entire lymph system. Such a segmentation determines which voxels of the image data belong to which structure, and which do not, and so individual structures can thereafter be selected without great complexity.

In the meantime, the most diverse (e.g. model-based) methods have been developed for being able to carry out a fully-automatic segmentation of such functional structures in three-dimensional image data. An example of this is found, inter alia, in the article "Hierarchical parsing and semantic navigation of full body CT data" by S. Seifert, A. Barbu, S. K. Zhou, D. Liu, J. Feulner, M. Huber, M. Sühling, A. Cavallaro, D. Comaniciu; Proceedings of the SPIE, volume 7259, pp. 725902-725902-8 (2009), the entire contents of which are hereby incorporated herein by reference.

Moreover, it is preferable for structure selection data to be determined thereafter in a subsequent step (but also in parallel or preceding it if necessary) for fixing functional structures to be visualized. That is to say this step determines which structures, for example which organs or skeleton structures, should even be visualized in the volume-viewing image to be generated and which should not. By way of example, the structure selection data can be determined by registering commands that were entered via a user interface. However, this data can also be determined automatically, e.g. from a database, for example as a function of a clinical question underlying the volume-viewing image generation.

At least one volume-viewing image is subsequently determined from the three-dimensional data on the basis of the segmented functional structures and the structure selection data. That is to say, for example, a scene to be visualized is determined first, in which scene the viewing direction from which the group of functional structures to be visualized should be observed is defined, and a volume-viewing image illustrating this scene is subsequently calculated. Finally, the determined volume-viewing image is output, for example to a storage medium and/or an image output arrangement such as e.g. a display or a printer, etc.

The advantage of the method according to at least one embodiment of the invention is that, by way of a simple selection of structures to be visualized, the preceding multiple structure segmentation allows the discovery or generation of the fitting volume-viewing images in a fully-automatic, semi-automatic or manual fashion, which volume-viewing images present the best information relating to the structures of interest. Laborious freeing of the individual structures with the aid of punch tools is no longer mandatory in this case.

A significant amount of time generally passes in any case between the recording of the raw measurement data in the medical imaging system with the subsequent reconstruction of the three-dimensional image data and the observation of the images and the diagnosis by a radiologist. This time can be used for segmenting the functional structures. There must only be sufficient computational capacity available. In the process, all relevant functional structures, for example all individual organs, vessels and bone structures, are preferably segmented in at least one predefined region of interest in the body, and so these structures can be displayed in a separate fashion from other structures. Here, the region can be defined as a function of a clinical question underlying the examination. By way of example, this can be all organs, bone structures and vessels of the abdominal region or the chest region, etc.

An image-processing device according to at least one embodiment of the invention for carrying out such a method firstly requires an image data interface for receiving the three-dimensional image data, and secondly requires a segmentation arrangement for segmenting a plurality of different functional structures of the body in the three-dimensional image data. Furthermore, the image-processing device requires a selection-data determination unit for determining structure selection data for fixing functional structures to be visualized. This can also be a type of interface by means of which selection data in the form of selection commands entered by an operator is registered, or an interface for receiving such data from a network or a database. The image-processing device moreover requires an image determination unit for determining a volume-viewing image from the three-dimensional image data on the basis of the segmented functional structures and the structure selection data, and an output interface for outputting the volume-viewing image, for example to a storage medium and/or an image output arrangement.

A multiplicity of the components of the image-processing device can be implemented in the form of software modules on a suitable computational unit or on a system of a plurality of computational units. This particularly holds true for the segmentation arrangement and the image determination unit. However, it is also possible for the selection-data determination unit and the image data interface and the output interface to be at least in part designed in the form of software components. An implementation to the greatest possible extent in the form of software modules is advantageous in that already existing image-processing devices can also be upgraded more easily in order to operate according to at least one embodiment of the invention. It is expedient in this case for e.g. a suitable graphical user interface to be available, which can also be used by the individual software components, for example the selection-data determination unit, if an operator should enter structure selection data. In this respect, at least one embodiment of the invention can also be achieved by a computer program product that can be loaded directly into a storage medium of an image-processing device, with program code means for executing all steps of the method according to at least one embodiment of the invention if the program product is executed on the image-processing device.

The dependent claims and the further description each contain particularly advantageous developments and refinements of embodiments of the invention, wherein the image-processing system according to at least one embodiment of the invention can also be developed in an analogous fashion.

In a particularly preferred development of at least one embodiment of the method, it is possible for a very specific structure, for example a very specific organ or part of an organ, to be defined as a target structure. For this, the structure selection data preferably already comprises target-structure selection data for fixing the target structure. That is to say it is not only an overall number of structures to be visualized that is fixed, but a specific target structure is also determined within these structures to be visualized, which target structure for example then is situated in the center of the generated volume-viewing image or is otherwise taken into account in a particular fashion during the generation of the volume-viewing image.

This target-structure selection data can likewise be determined via a user interface. By way of example, in order to register structure selection data including the target-structure selection data, an operator can show activatable representation illustrations of the segmented structures by means of a user interface. These representation illustrations are simply e.g. schematic drawings of the respective organs, vessels or skeleton structures that allow the operator unambiguously to identify the relevant structure. By way of example, the representation illustrations can be displayed on a graphical user interface with a number of virtual buttons, and the user can activate the buttons by mouse-click. The structures can likewise be illustrated within a pictogram, wherein regions that can be activated by mouse-click within this pictogram are assigned to the individual organs, skeleton structures or vessels.

More particularly, it is also possible for the target structure to also be selected in this fashion, for example by selecting the functional structures to be visualized in general by one button in the normal case and by selecting a target structure by a coordinated action of two buttons. It is likewise possible that the structures to be visualized in general and the target structure are selected in different successive method sections.

In one variant, in order to register target-structure selection data a volume display of at least the functional structures to be visualized is shown to an operator on the basis of the three-dimensional image data. In this visualization, the target structure can then be selected by means of a graphical user interface, for example by displacing a cursor onto the desired structure and by performing a mouse-click or the like. Then a search beam is emitted by the cursor in the viewing direction and the structure hit first by the search beam in the viewing direction is selected.

It is preferable for it to be possible to assign individual transfer functions to the segmented functional structures. That is to say every organ, every bone structure, etc. is assigned a certain transparency and color. The advantage of this is that certain organs or skeleton structures are still visibly present for the diagnosing person for the purposes of orientation, but in principle it is possible to see through these to see the relevant structures to be diagnosed in actual fact. By way of example, each individual voxel within a three-dimensional volume display, which voxel is usually linked to a certain grayscale value, can respectively be assigned a color and a transparency by a table in order to define the transfer function. Here the color reproduces the information from the grayscale value and the transparency is freely available in order to make it possible to see through the respective voxel within the 3D volume display.

In a particularly preferred variant of at least one embodiment, a viewpoint is determined automatically as a function of the structure selection data, more particularly as a function of the target-structure selection data (i.e. as a function of the respectively selected target structure). Here, the viewpoint is advantageously determined automatically such that the respective target structure, possibly also a plurality of target structures or a certain part of interest of a target structure, is displayed such that the most information in respect thereof can be seen in the image.

There are a number of approaches for automatically selecting a viewpoint (automatic virtual camera positioning).

A viewpoint is preferably determined automatically within the scope of a model-based search using at least one viewing sphere, in which a view quality value is coded in respect of at least one view-relevant parameter as a function of the viewing direction. That is to say the possible viewpoints are distributed on a so-called "viewing sphere", e.g. the surface of a sphere, that for example surrounds the volume of interest, and the possible viewpoints are evaluated. By way of example, the center of this viewing sphere can be the focus of the target structure, more particularly an organ focus, a point of interest on the surface of the target structure specified by the operator, or else a point determined automatically on the basis of the underlying clinical question (e.g. the outlet of the kidneys to the ureter in the case of an examination relating to kidney stones in order to monitor whether the ureter is blocked here, or a tumor to be observed in a repeat examination of an organ afflicted by tumor).

The coding of the view quality value on such a viewing sphere can be carried out such that, for each point on the viewing sphere, the radius to the center of the viewing sphere is selected to be ever larger as the view quality value increases at this viewpoint. This generates a deformed viewing sphere in which the viewpoints situated furthest to the outside have the best view quality in respect of the prescribed view-relevant parameter.

Various parameters could be used as view-relevant parameters. A defined preferred viewing direction that for example can be preselected by the operator or can be prescribed for certain clinical questions can be a view-relevant parameter. The shape, i.e. the form and possibly the dimension, of the target structure can be another view-relevant parameter. A further preferred view-relevant parameter is the visibility of a focus in the target structure.

Furthermore, the visibility of the surface of the target structure can also be taken into account in the automatic determination of a viewpoint. By way of example, the visibility of the surface can be taken into account such that a weighted sum of the voxels of the structure that are visible in the respective viewing direction is defined. If work is only carried out according to this parameter, the result is a camera position with a maximum number of visible voxels. Depending on the properties of the structure of interest, such an evaluation can lead to a maximized surface, but also to inexpedient viewpoints. It is particularly preferable for a plurality of viewing spheres for different view-relevant parameters to be combined together to determine a viewpoint. The combination can in this case be brought about using various combination operators, for example an addition operator, a multiplication operator, a limit value operator or the like.

An option for generating such viewing spheres and combinations of viewing spheres using different operators is described in more detail in the article "LiveSynch: Deformed Viewing Spheres for Knowledge-Based Navigation" by P. Kohlmann, S. Bruckner, A. Kanitsar and M. E. Grolier, in IEEE Transactions on Visualization and Computer Graphics, Volume 13, number 6, 2007, pages 1544 to 1551, the entire contents of which are hereby incorporated herein by reference. The methods described therein can also be applied within the scope of the embodiments of the present invention.

In a particularly preferred variant of at least one embodiment, a start viewpoint is first of all determined according to the above-described method by combining a plurality of viewing spheres. The viewpoint is then actually determined in a region around the start viewpoint taking into account the visibility of the surface of the target structure.

By way of example, a preferably freely definable or configurable number of candidate viewpoints can preferably be fixed in a region around the start viewpoint for this purpose. Search beams are then emitted to each of these candidate viewpoints from various surface points or voxels in a defined relevant region of the surface of the target structure. These search beams are then analyzed as to whether they reach the respective candidate viewpoint.

This method of taking into account the surface visibility in a region around a start viewpoint can also be advantageous when selecting the start viewpoint independently of the procedure.

In the process, it is also possible for transfer functions of other visualized organs to be taken into account. By way of example, if a small transfer function is assigned to another organ, i.e. said organ is illustrated opaquely, then the search beam may not reach the candidate viewpoint. Likewise, the transfer function can be suitably taken into account in the analysis if the organ is illustrated in a transparent fashion, i.e. although said organ is also visualized in the image, it only limits the visibility of the target structure but does not completely prevent the visibility thereof. A viewpoint is then selected from the candidate viewpoints on the basis of a result of the entire analysis.

Depending on the clinical question, it may be desirable to place a so-called "clip plane". Such a clip plane is a slice plane through the visualized structures, in which everything that is situated in front of the clip plane as seen from the viewpoint is automatically removed from the image. By way of example, if such a clip plane is situated within an organ, a slice of this organ is displayed at this location and, starting from this slice plane and going away from the viewpoint, the further contours are displayed as a three-dimensional exterior view.

By way of example, such a cross section through an organ can be fixed by an operator with the aid of a graphical user interface. However, in a preferred variant, the invention also allows the clip plane to be placed in front of a certain structure, i.e. a specific organ or a vessel, in order to free it automatically. In order to fix the clip plane along a connection axis running from the viewpoint to a target point in the target structure, a plane intersection can be fixed for this purpose at a distance between a target structure surface and the viewpoint. The clip plane is then fixed such that it is orthogonal to the connection axis and the plane intersection is situated in the clip plane. The target point can generally be the focus of the target structure or a point set by a user. The distance between the plane intersection and the target structure surface can be relatively short in this case, but should preferably be at least that long that the entire organ is situated behind the clip plane when seen from the viewpoint such that the organ is completely freed without being cut by the clip plane.

It is particularly preferable for various scenarios to be predefined within the method according to at least one embodiment of the invention, with specific structure selection data and/or individual transfer functions for functional structures and/or view-relevant parameters being assigned to said scenarios. It is also possible for more of the above-described parameters to be assigned to these scenarios, e.g. which view-relevant parameters are used when defining viewing spheres and how the various viewing spheres are combined, for example what weighting is used for the view-relevant parameters. Parameters for automatically fixing clip planes can likewise already be assigned hereby.

The various predefined scenarios can be defined for various clinical questions. It is then preferably possible for at least one predefined scenario to be automatically selected on the basis of patient-specific and/or examination-specific data. Such patient-specific and/or examination-specific data can for example be available within a radiology information system (RIS). In particular, these can be examination requested data (so-called requested procedures), by which the examinations to be carried out are defined on the respective imaging system. If a predefined scenario is selected on the basis of the data available in the RIS, the assigned structure selection data, individual transfer functions, view-relevant parameters etc. can be used to generate the fitting volume-viewing images in a fully-automatic fashion from the three-dimensional image data, which volume-viewing images the diagnosing person is very likely to need for diagnosing in the case of the respective clinical question.

BRIEF DESCRIPTION OF THE DRAWINGS

The invention will be explained in more detail hereinbelow on the basis of example embodiments with references to the attached drawings, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the following example embodiment, the assumption is made (without limiting embodiments of the invention thereto) that the structures to be visualized are organs in each case, wherein a vessel or a functional part of a vessel, for example the abdominal aorta, is likewise referred to as an organ. It is for this reason that hereinbelow the term "organ" is usually used instead of the term "functional structure".

Figure 1:
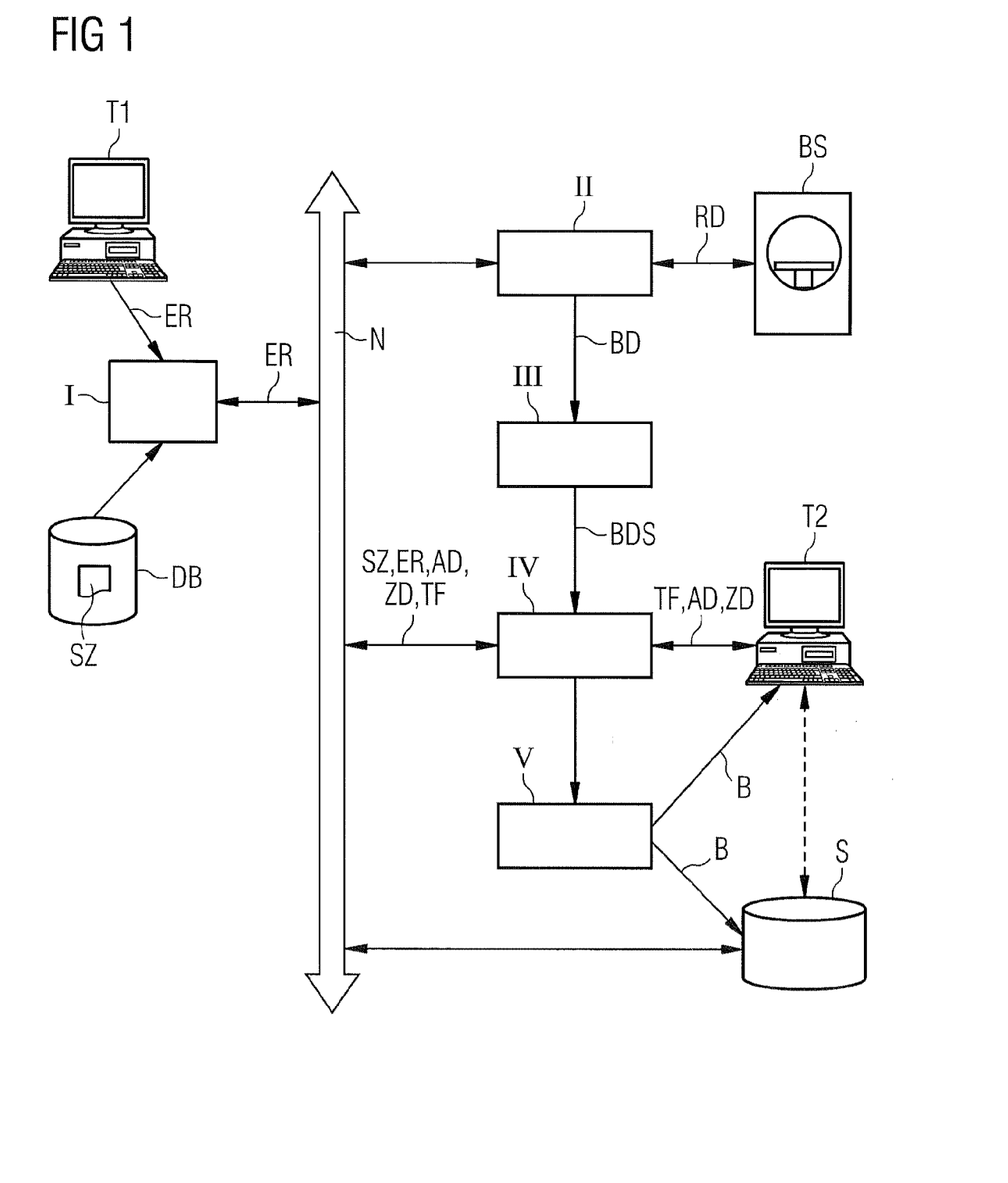
FIG. 1 shows a schematic illustration of a possible progression of the method according to an embodiment of the invention.

In the subsequent example embodiment, the assumption is furthermore made that patient data is firstly recorded in a step I for a clinical examination and an examination request ER is defined, which firstly contains patient-specific information such as name, age and sex, and secondly contains examination-specific information, for example with what previous diagnosis a patient has arrived and what specific examinations and diagnoses should be carried out. This data can be entered at e.g. any terminal T1. At least some of the data can also be transmitted from a referring medical practitioner over a preferably secure channel of a network, or can be transferred electronically by other means. In a second step II, this data is then used via a network N in an imaging system BS, for example a computed tomography scanner or a magnetic resonance imaging scanner, in order to carry out the measurements defined in the examination request ER. For this, the necessary raw data RD is acquired by the imaging system BS and the image data BD is likewise reconstructed therefrom in step II. Here this is three-dimensional image data, with it being possible for the individual voxels for example to have been recorded layer-by-layer or else directly in the form of a volume measurement.

According to an embodiment of the invention, this image data BD is first of all segmented in a step III. Herein all organs of the relevant region are preferably segmented individually. The segmented structures or organs are marked unambiguously so that they can be identified thereby. This can be brought arbitrarily about in the form of a suitable name for the respective organ such as "liver", "left kidney", etc. but also by using reference numerals or the like. All that is essential is that the segmented organs can be selected automatically or by an operator in the subsequent method in order then to visualize the associated segmented structures, i.e. all voxels belonging to the respective structure, to remove said segmented structures from a visualization or to provide said segmented structures with a specific transfer function, i.e. a certain transparency.

In a further step IV, structure selection data AD, target-structure selection data ZD and possibly transfer functions TF are subsequently defined. This can be brought about with the aid of a user terminal T2, as will be explained in more detail below. However, it is also possible to gather this data via the network N, for example with the aid of the data entered into the associated examination request EZ in the RIS. More particularly, it is possible for some of the data or even all of the data for the viewing-image generation already to be defined in a scenario SZ. For this, it is possible for various scenarios SZ to be stored in a database DB, and such a scenario SZ is for example selected in step I during the definition of the examination request on the basis of the clinical question. All data necessary to identify the scenario and/or the individual data AD, ZD, TF assigned to the scenario SZ is then either transmitted with the examination request ER to the computational units used thereafter for automatically generating the volume-viewing images, or, in step IV, a scenario SZ or at least individual parameters AD, ZD, TF are determined from the database DB on the basis of the examination request EZ.

Various options available to an operator for selecting the structures to be visualized and/or a target structure via a terminal T2 are explained below on the basis of FIGS. 11 and 12.

Figure 11:
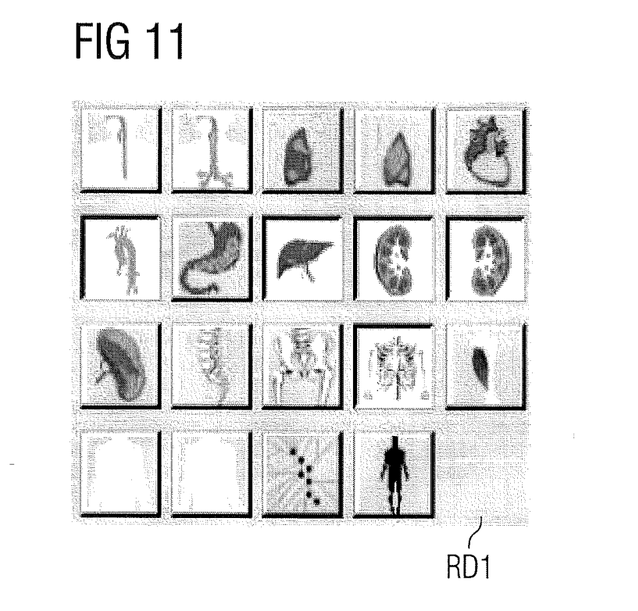
FIG. 11 shows a schematic illustration of a graphical user interface in the form of virtual buttons for selecting structures to be visualized and a target structure.

One option includes a number of virtual buttons being displayed on a display of the terminal, as shown in FIG. 11. Each of these virtual buttons contains a representative illustration, for example a schematic drawing, of the organ or the bone structure. The operator can then click the virtual buttons with the aid of a mouse pointer and hence select certain organs or bone structures that are intended to be visualized thereafter. This allows very simple acquisition of structure selection data AD. For example, in the representation illustration RD1 in FIG. 11, the organs on the buttons illustrated in a depressed fashion (i.e. the brightly stored organs) have already been selected, while the organs on the buttons illustrated in an elevated fashion have not yet been selected and would therefore not be illustrated in the volume-viewing image to be produced.

Figure 12:
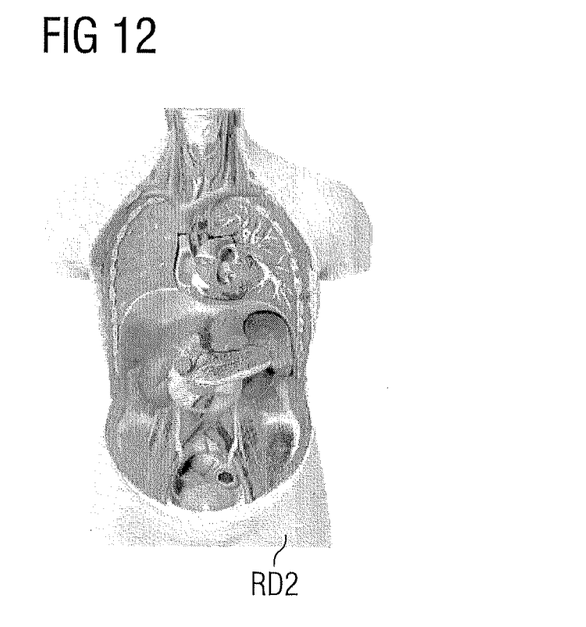
FIG. 12 shows a schematic illustration of a graphical user interface in the form of a pictogram with activatable regions for selecting structures to be visualized and a target structure.

FIG. 12 shows a different variant for an activatable representation illustration RD2. Here, the user selects which organs should be visualized and which organs should not be illustrated by means of a click on the illustrated pictogram. In the process, the pictogram can contain sensitive zones that preferably correspond as precisely as possible to the multiple organ-structure segmentation carried out in advance. That is to say that the segmented liver for example has its own zone that corresponds to the image display of the liver in the pictogram. Corresponding statements hold true for the kidneys, the abdominal aorta, the ribs, the heart, the intestines, etc.

Additionally, an operator can place the focus onto a target organ of particular interest in order to select structures to be visualized within the organs to be visualized. More particularly, the method according to the invention then allows an automatic placement of the optimum viewpoint on the focused target organ.

It is preferable for the following interactions for focusing on a particular organ to be possible in the process:

By way of example, within the selection method as defined above on the basis of FIGS. 11 and 12, it is possible to determine whether the selected organ is simply an organ to be visualized or the target organ by simultaneously pressing an additional button, e.g. a shift key.

A further option includes the organs to be visualized being shown in a volume display. The operator can click directly onto the target organ with a mouse pointer in this display. The organ is then detected by the emission of a search beam in the viewing direction onto the selected point, and that organ is selected, whose associated voxel is reached first by the search beam.

However, as already explained above, it is not only the organs to be visualized but also the target organ that can be predefined within a scenario.

Once all structures to be visualized and, if appropriate, the target structure have been selected, the volume-viewing image is actually determined in step V.

For this, the best view onto the target structure, more particularly onto a target organ, is first of all preferably determined taking into account the other visualized structures. In the illustrated example embodiment, the most expedient viewpoint is determined within the scope of a model-based search with a subsequent correction by a locally-delimited surface-visibility analysis.

Here, the model-based search contains the coding and combination of view-relevant parameters within the scope of viewing spheres, in a similar fashion as already explained in the article by P. Kohlmann et al. cited above. Herein, the following criteria or view-relevant parameters are taken into account overall.

1. The Preferred Viewing Direction:

Depending on the available data record it is possible for favored viewing directions onto the volume display to be defined. Here the operator or the subsequent diagnosing person, who should observe the image, can preconfigure their favored viewing directions for certain body regions or certain clinical questions. By way of example, this can be brought about by a manual positioning of the virtual camera and by storing the position in a configuration mode.

Figure 5:
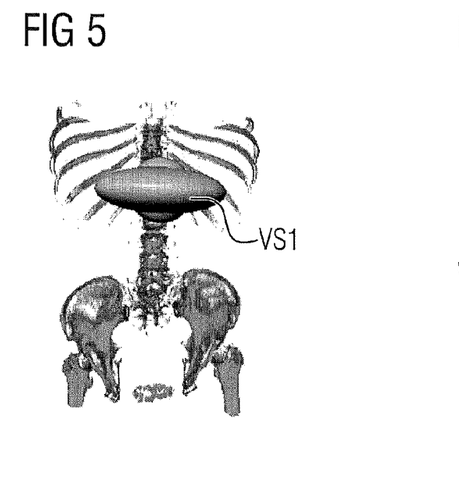
FIG. 5 shows an illustration of a viewing sphere taking into account a preferred viewing direction.

As an example, a viewing sphere VS1 is illustrated in FIG. 5, in which the normal direction, i.e. the perpendicular direction, with respect to the head-foot axis of the patient is coded as being preferred. This is why the viewing sphere has a shape such that all viewpoints situated precisely perpendicular to the head-foot axis of the patient are situated further away from the central point of the viewing sphere than the points situated parallel to the head-foot axis of the patient.

2. The Shape of the Organ:

The target organ can be analyzed with respect to its dominant spatial extent by using principal component analysis. The preferred viewpoints are then coded in a viewing sphere such that the view in the normal direction onto the largest organ extent is favored.

Figure 6:
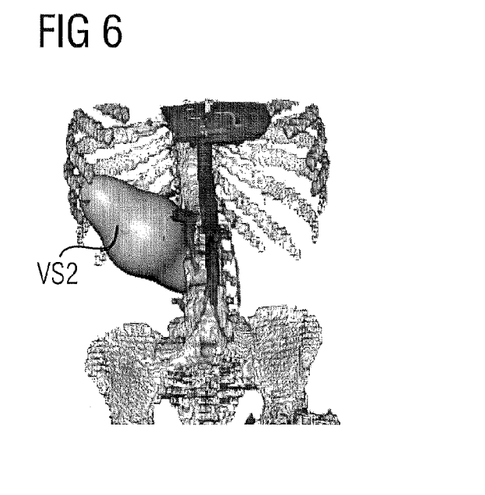
FIG. 6 shows an illustration of a viewing sphere taking into account the shape of an organ.

FIG. 6 shows an example of the viewing sphere in respect of the view-relevant parameter "organ shape" of a kidney.

Figure 7:
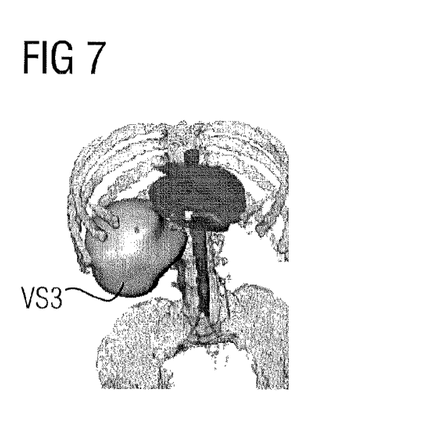
FIG. 7 shows an illustration of a viewing sphere taking into account the visibility of an organ focus.

3. The Visibility of the Structure Focus:

In order to allow an optimal view onto the target organ, beams are emitted from the focus of the segmented target organ in all spatial directions. In the process, the opacities of the voxels that are passed through are integrated. Here, the opacities are given by the transfer function of the individual organs. These transfer functions can preferably be predetermined for each individual segmented organ as described above and more particularly can already be stored for certain scenarios. Here, which organs should even be visualized in the planned volume-viewing images is taken into account. Masked organs are considered to have an opacity of 0, i.e. they are completely translucent. Surrounding organs that should be visualized are taken into account by the opacity of their specific transfer function. Alternatively, it is also possible to take into account all surrounding organs with an opacity of 1, i.e. they are completely opaque. If a beam reaches a voxel with an opacity of 1, the beam is terminated and coded with a minimal visibility value in the viewing sphere. If the opacity lies between 1 and 0, the assumption is made that the search beam is restricted in respect of the visibility, which can likewise be coded within the viewing sphere by correspondingly setting the distance between the respective viewpoint on the viewing sphere and the center of the viewing sphere.

Such a viewing sphere taking into account the visibility of the organ focus is illustrated in FIG. 7 using the example of a liver with the surrounding covering organs and bone structures.

The viewing spheres described above can be linked with the aid of operators. Three different operators are schematically illustrated in FIG. 8.

The upper image shows an addition operator, in which the values of the combined individual viewing spheres are simply added for all viewpoints on the viewing sphere.

Figure 8:
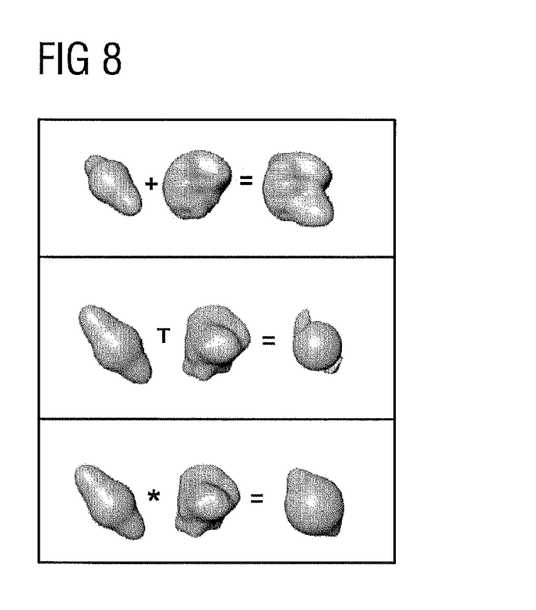
FIG. 8 shows a schematic illustration of operators for linking viewing spheres.

A limit value operator is illustrated in the center of FIG. 8. Here, the radii of the right operand are used in the result if the left operand has a radius at this position that is larger than a prescribed threshold. This operator can implement separation criteria very well.

A multiplication operator is illustrated in the lower column of FIG. 8. Here small radii in one of the operands have a large effect on the corresponding position in the result. Thus, a large radius in the result means that a good camera position is induced at this position on all viewing spheres that have been taken into account.

Reference is made to the article by Kohlmann et al. for the precise definition and implementation of such operators.

The individual viewing spheres can also be weighted during the combination thereof in order to adapt their influence. Examples of this will additionally be provided further below on the basis of FIGS. 3 and 4.

As already explained above, it is possible for the viewpoint determined thereby to be corrected in respect of the visibility of the organ surface. This is brought about in a local surface-view analysis.

For this, a start viewpoint SAP is first of all selected in a pre-positioning step, preferably with the aid of the above-described method taking into account a combination of the various viewing spheres. In a subsequent fine positioning step, the optimum viewpoint is then selected within the surroundings of this start viewpoint. In the process, a configurable number of candidate viewpoints KAP are selected around the start viewpoint SAP. A simple example thereof is illustrated schematically in FIG. 9. A surface analysis of the surface O of the organ of interest is carried out for each of these candidate viewpoints KAP (including the start viewpoint SAP); this is done to select the viewing position thereafter such that the visible surface O is maximized. For this, search beams from all surface points OP in a region in the direction of the camera positions or viewpoints to be evaluated are taken into account. By way of example, these can be all surface points that are situated within an angle $\alpha$, starting from a connection axis between the start viewpoint SAP and the organ focus OSP. By way of example, the surface points OP are the centers of the surface voxels of the segmented organ. Here, care is preferably taken that the voxels are isometric in the fewest cases. The resolution in the z-direction is usually lower than in the x- or y-direction. The result of this is that the visible area of a voxel varies according to the viewing direction. It is therefore preferably determined from which surface of the voxel the search beam emanates. The value of this surface is then also included in the evaluation. The x- and y-resolutions are generally identical in volume data records. The problem can therefore be reduced to determining whether the search beam emanates from the upper or lower surface, or from one of the side surfaces. In order to determine the emanating surface, the angle between a plane running through the focus of the voxel, parallel to the base surface, and the search beam is considered.

Figure 9:
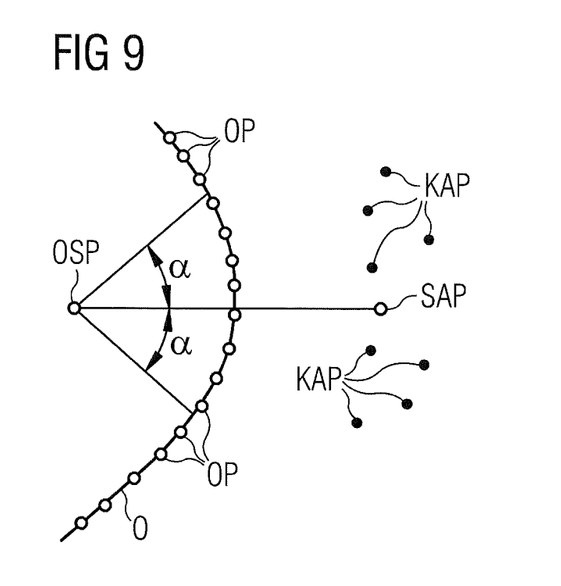
FIG. 9 shows a schematic illustration of a limited organ surface analysis for finding an optimum viewpoint.

As mentioned, this surface analysis is limited to the local neighborhood of promising candidate viewpoints KAP because a complete evaluation of the visible surface 0 of the organ for each possible viewpoint would be too expensive in computational terms and thus would prevent real-time interaction.

Figure 10:
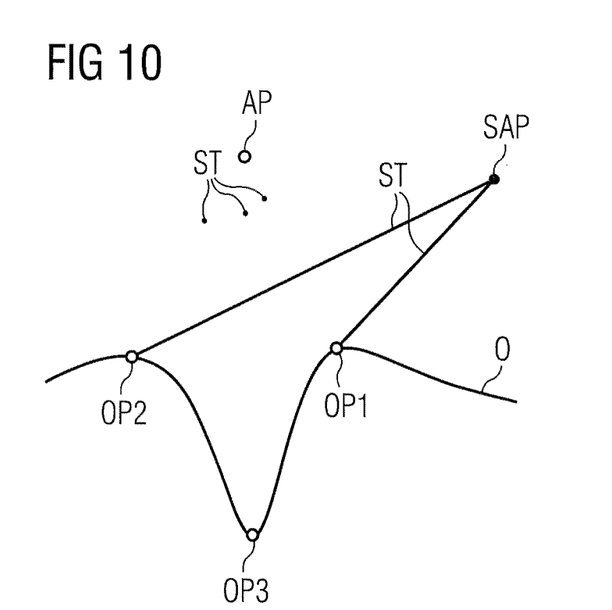
FIG. 10 shows an illustration of the different visibility of surface portions of an organ from various viewpoints.

FIG. 10 shows a simple example of how the camera position can be improved by such an analysis. A start viewpoint SAP from which a large part of the organ surface is clearly visible was first of all selected in this case. Two search beams ST, which run from two surface points OP1, OP2 to this start viewpoint SAP, are also indicated. However, there is no search beam which leads to this start viewpoint from the base of a fold in the surface O, i.e. from the organ surface point OP3. However, a viewpoint AP was found within the scope of the local surface-view analysis from which search beams ST lead to all three surface points OP1, OP2, OP3, i.e. this viewpoint AP also ensures an optimal view into the fold of the organ surface O.

Figure 3:
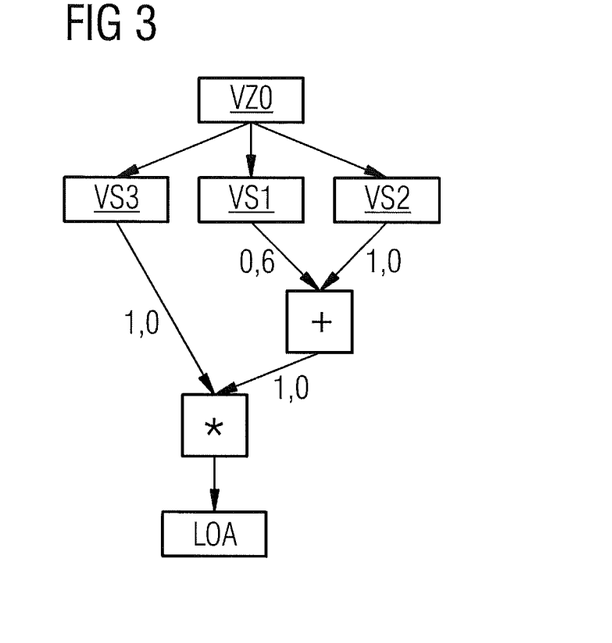
FIG. 3 shows a possible variant for a method for determining an automatic viewpoint in respect of an observation of an organ surface.
Figure 4:
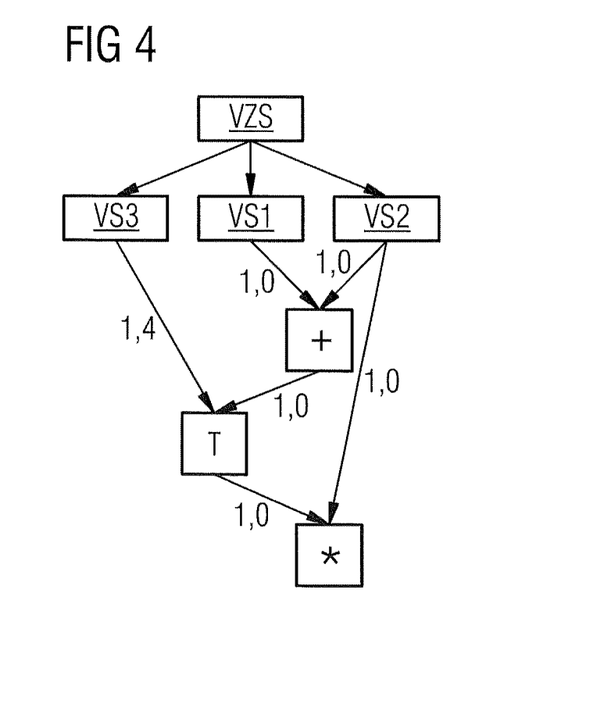
FIG. 4 shows a possible variant for a method for determining an automatic viewpoint in respect of an observation of the cross-section through an organ.

FIGS. 3 and 4 illustrate how different optimum viewpoints can be found by different weighting and linking of various viewing spheres, and by possibly applying local surface-view analysis depending on the clinical question or a given visualization goal.

In FIG. 3, a visualization goal VZO is firstly defined, in which the point is preferably to diagnose the organ surface. For this, the viewing spheres VS1, VS2, VS3 are first of all defined by the above-described criteria or the view-relevant parameters 1 to 3. Then the viewing sphere VS1 in respect of the view-relevant parameter "orientation" and the viewing sphere VS2 in respect of the view-relevant parameter "shape" are added, with the orientation being weighted with a factor of 0.6 and the shape with a factor of 1.0. The result is then combined by multiplication with the viewing sphere VS3 in respect of the view-relevant parameter "structure focus visibility", wherein the result of the addition and the further viewing sphere VS3 are respectively included with the same weighting with a factor of 1.0. A local surface-visibility analysis LOA is subsequently carried out as described above, taking into account the optimum viewpoint determined thereby as a start viewpoint.

FIG. 4 assumes a visualization goal VZS in which an organ slice should be visualized. The three viewing spheres VS1, VS2, VS3 of the relevant organ in this case are also generated at first again. Here, there is likewise firstly an addition of the viewing sphere VS1 for the orientation and the viewing sphere VS2 for the organ shape, but with an equal weighting factor of 1.0 in this case. The result is then combined with the viewing sphere VS3 in respect of the visibility of the organ focus by means of a threshold operator, wherein the result of the addition obtains a weighting factor of 1.0 and the further viewing sphere in respect of the visibility of the organ focus obtains a weighting factor of 1.4. Subsequently, the viewing sphere obtained thereby (with a weighting factor of 1.0) is multiplied with the original viewing sphere VS2 in respect of the organ shape (which is again included with a weighting of 1.0).

Once an optimal viewpoint has been found, it can be expedient to place a clip plane, depending on the clinical question. This can be brought about in either a fully-automatic fashion or a semi-automatic fashion, e.g. by way of a simple operator interaction.

Two cases should be distinguished when placing such a clip plane:

1. The clip plane is placed in front of an organ: In this case, a clip plane further improves the view onto a target organ by removing bothersome image data situated in front of the clip plane as seen from the camera position. Here, for the purpose of automatic freeing, a beam from the focus of the organ in the direction of the current viewpoint can be analyzed in order to find the organ surface in this direction. At the point at which the search beam passes through the organ, the beam is elongated by a small amount. The end of the beam is then used as a point for defining the clip plane, which is positioned in the normal direction with respect to the beam. This automatically frees the respective organ in a simple fashion. Alternatively, the user can also fix the intersection point at which the clip plane is placed onto the search beam with the aid of a graphical user interface.

2. An organ cross section is fixed with the aid of a clip plane: In order to visualize an organ slice, an operator can for example specify any point through which the clip plane should pass by clicking on a two-dimensional view that is output in parallel. The orientation of the clip plane is then for example again calculated automatically in respect of the viewpoint in the three-dimensional volume-viewing image and is visualized there accordingly. In such a slice, the grayscale value information of the respectively cut organ is displayed on the clip plane by way of known methods.

The clip plane can preferably be connected to an interactive element in both visualization goals, and so the operator can tilt and displace the currently illustrated clip plane by means of a graphical user interface.

If the desired volume-viewing images B are generated in step V (see FIG. 1) in the form of, for example, screenshots, these images B can either be displayed immediately on the terminal T2 and/or be stored in a mass storage medium S for later diagnosis. More particularly, the screenshots saved in this fashion can also again be queried from the storage medium S via the network N and can for example be viewed by the radiologist at any diagnosing station.

Figure 2:
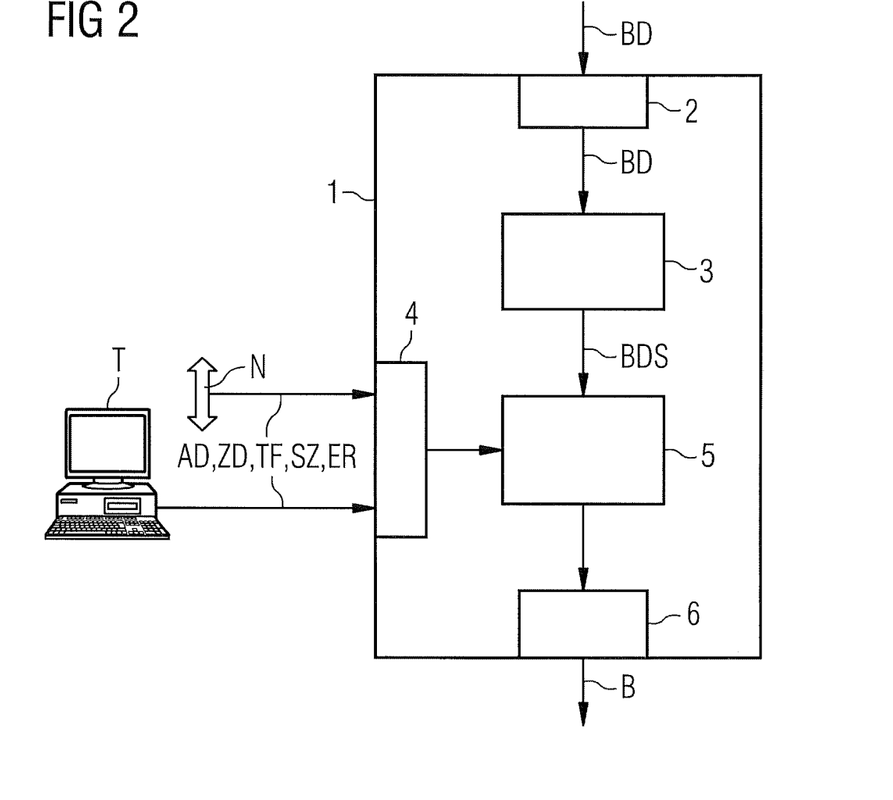
FIG. 2 shows a schematic illustration of an example embodiment of an image-processing system according to an embodiment of the invention.

FIG. 2 shows in a roughly schematic fashion an image-processing system 1 by which this method can be carried out. Here, the image-processing system 1 has an image data interface 2, by which the image-processing system can receive image data BD from, for example, a reconstruction arrangement or a mass storage medium in which the image data for a particular examination request had previously been stored. The image-processing system 1 moreover has a segmentation arrangement 3, in which the various structures, more particularly organs, are segmented according to an embodiment of the invention.

The structure selection data AD and the target-structure selection data ZD for fixing functional structures to be visualized and the target structure, and possibly additional relevant data for the imaging as described above are determined in a selection-data determination unit 4, which can for example also be designed as a user interface with a connection to a terminal T or as an interface to a network N. It is also possible for all software modules or the like to be implemented in this unit in order to define the necessary data as explained further above on the basis of FIG. 1 in step IV.

Here, a central module of the image-processing system 1 is an image determination unit 5, which generates a volume-viewing image B, or generally a plurality of volume-viewing images B, from the three-dimensional image data BD on the basis of the segmented functional structures and the structure selection data AD, which volume-viewing image(s) can then be output via an output interface 6 of the image-processing system 1 to a storage medium and/or to an image output arrangement such as a display or a printer.

The image-processing system 1 is illustrated here in the form of a contiguous block. However, in principle it is also possible for the components of the image-processing system 1 to be implemented on a plurality of locally separate partial systems. In particular, the segmentation arrangement 3 can for example be implemented on a different computer than the selection-data determination unit 4 and the image determination unit 5. This is expedient to the extent that the segmentation requires a relatively high computational capacity. In this respect, a special computer could be reserved for this, which takes on the image data BD on request and undertakes the segmentation before there is further analysis of the image data BD, for example during a waiting period before an operator even considers this data.

The image data that has been completely segmented BDS is then taken on for processing and the computational unit is free to segment other image data during the further image processing.

The method according to an embodiment of the invention offers the option of selectively fading organs of interest into and out of a volume-viewing illustration, either in a semi-automatic fashion, merely by means of simple, intuitive user interactions, or even in a fully-automatic fashion. The method thus permits the fully-automatic generation of screenshots of predefined 3D illustrations with optimum information content. By using RIS information, it is possible, depending on the clinical question, for the system automatically to select certain scenarios, i.e. presets of parameters for the visualization, more particularly for organs to be visualized, a target organ, transfer functions, preferred viewing positions, etc.

In addition to the multiple structure segmentation, the preferred option of also assigning defined individual transfer functions to the individual structures, more particularly organs, and assigning a certain transparency to the latter is particularly advantageous in this case. A local surface-visibility analysis can additionally minimize the self-cover of the structure of interest.

In addition to the simple provision of an optimum start point for generating volume-viewing images depending on given three-dimensional image data and certain prescribed clinical questions, for example based on RIS information, the method prevents the need for always carrying out the same steps manually for generating optimal volume-viewing images for repeated questions. This also increases the acceptance for various applications, such as intervention planning.

Finally, reference is once again made to the fact that the method and the image-processing system described in detail above are merely preferred example embodiments that can be modified by a person skilled in the art in a wide variety of ways without leaving the scope of the invention provided it is allowed by the claims. For the sake of completeness, reference is also made to the fact that the use of the indefinite article "a" and "an" does not exclude the possibility of the relevant features being present a number of times. Likewise, the terms "unit" or "module" etc. do not preclude these from consisting of a plurality of components which can if necessary also be spatially distributed.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating at least one volume-viewing image based upon three-dimensional image data of an interior of a body generated by way of a medical imaging system, the method comprising:
    obtaining the three-dimensional image data from the medical imaging system;
    segmenting, by one or more processors, a plurality of different functional structures of the body in the three-dimensional image data;
    determining, by the one or more processors, structure selection data for fixing at least one functional structure to be visualized and at least one functional structure not to be visualized and determining a total number of the at least one functional structure to be visualized;
    fixing, by the one or more processors, the at least one functional structure to be visualized and the at least one functional structure not to be visualized using the structure selection data;
    obtaining, by the one or more processors, a plurality of different viewing spheres associated with the at least one functional structure to be visualized, each of the plurality of different viewing spheres associated with a view-relevant parameter;
    combining, by the one or more processors, the plurality of different viewing spheres;
    determining, by the one or more processors, a start viewpoint of the at least one functional structure to be visualized based on the combined plurality of different viewing spheres and a visible surface of the at least one functional structure to be visualized;
    determining, by the one or more processors, a plurality of viewpoints in a region around the start viewpoint, the plurality of viewpoints including the start viewpoint;
    determining, by the one or more processors, a plurality of candidate viewpoints of a region of the visible surface of the target structure from the plurality of viewpoints, a number of the candidate viewpoints being less than a number of the plurality of viewpoints and the region of the visible surface being less than the visible surface;
    selecting, by the one or more processors, one of the plurality of candidate viewpoints;
    generating, by the one or more processors, the at least one volume-viewing image from the three-dimensional image data with respect to the selected viewpoint; and
    displaying, by the one or more processors, the generated at least one volume-viewing image including the region of the visible surface of the at least one functional structure to be visualized with respect to the selected viewpoint, wherein individual transfer functions are separately assigned to the segmented functional structures.

2. The method as claimed in claim 1, wherein the structure selection data comprises target-structure selection data for fixing a target structure.

3. The method as claimed in claim 2, wherein the determining structure selection data includes displaying a volume display of the at least one functional structure to be visualized on the basis of the three-dimensional image data.

4. The method as claimed in claim 2, wherein the determining the structure selection data includes displaying, activatable representation illustrations of the segmented structures via a user interface.

5. The method as claimed in claim 1, wherein the determining structure selection data includes displaying activatable representation illustrations of the segmented structures via a user interface.

6. The method as claimed in claim 1, wherein the view-relevant parameter includes at least one of,
    a viewing direction,
    a shape of a target structure, and
    a visibility of a focus or a point of interest in the target structure.

7. The method as claimed in claim 1, wherein the determining the at least one volume-viewing image includes determining a clip plane with respect to the selected viewpoint.

8. The method as claimed in claim 7, wherein the determining the at least one volume-viewing image includes,
    determining a plane intersection at a distance between the visible surface of the at least one functional structure to be visualized and the viewpoint, and the clip plane is orthogonal to a connection axis between the selected viewpoint and a point in the at least one functional structure to be visualized and the plane intersection is situated in the clip plane.

9. The method as claimed in claim 1, wherein at least one of the structure selection data, the individual transfer functions and view-relevant parameters are assigned to various scenarios.

10. The method as claimed in claim 9, wherein at least one scenario is automatically selected on the basis of at least one of patient-specific and examination-specific data.

11. The method of claim 1, wherein each of the plurality of different viewing spheres is associated with a different view-relevant parameter.

12. A method for generating at least one volume-viewing image onto a target structure based upon three-dimensional image data of an interior of a body generated by way of a medical imaging system, the method comprising:
- segmenting, by one or more processors, a plurality of different functional structures of the body in the three-dimensional image data, the target structure being one of the plurality of different functional structures of the body;
- obtaining, by one or more processors, a plurality of different viewing spheres associated with the target structure, each of the plurality of different viewing spheres associated with a view-relevant parameter;
- combining, by the one or more processors, the plurality of different viewing spheres;
- determining, by the one or more processors, a start viewpoint of the target structure based on the combined plurality of different viewing spheres and a visible surface of the target structure;
- determining, by the one or more processors, a plurality of viewpoints in a region around the start viewpoint, the plurality of viewpoints including the start viewpoint;
- determining, by the one or more processors, a plurality of candidate viewpoints of a region of the visible surface of the target structure from the plurality of viewpoints, a number of the candidate viewpoints being less than a number of viewpoints and the region of the visible surface being less than the visible surface;
- selecting one of the plurality of candidate viewpoints;
- generating, by the one or more processors, the at least one volume-viewing image of the target structure with respect to the selected viewpoint; and
- displaying, by the one or more processors, the generate at least one volume-viewing image including the region of the visible surface of the target structure with respect to the selected viewpoint, wherein individual transfer functions are separately assigned to the segmented functional structures.

13. The method as claimed in claim 12, wherein the candidate viewpoints are fixed in the region around the start viewpoint, and
the selecting includes,
- analyzing search beams for each candidate viewpoint, the search beams running from various surface points in the region of the visible surface of the target structure to the candidate viewpoints, and
- selecting the selected viewpoint from the candidate viewpoints based on the analyzing.

14. The method of claim 12, wherein each of the plurality of different viewing spheres is associated with a different view-relevant parameter.

15. An image-processing system for generating at least one volume-viewing image on the basis of three-dimensional image data of an interior of a body generated by way of a medical imaging system, the image-processing system comprising:
one or more processors configured to,
- receive the three-dimensional image data;
- segment a plurality of different functional structures of the body in the three-dimensional image data;
- determine structure selection data for fixing at least one functional structure to be visualized and at least one functional structure not to be visualized and determine a total number of the functional structures to be visualized;
- fix the at least one functional structure to be visualized and the at least one functional structure not to be visualized;
- obtain a plurality of different viewing spheres associated with the at least one functional structure to be visualized, each of the plurality of different viewing spheres associated with a view-relevant parameter;
- combine the plurality of different viewing spheres;
- determine a start viewpoint of the at least one functional structure to be visualized based on the combined plurality of different viewing spheres and a visible surface of the at least one functional structure to be visualized;
- determine a plurality of viewpoints in a region around the start viewpoint, the plurality of viewpoints including the start viewpoint;
- determine a plurality of candidate viewpoints of a region of the visible surface of the target structure from the plurality of viewpoints, a number of the candidate viewpoints being less than a number of the plurality of viewpoints and the region of the visible surface being less than the visible surface;
- select one of the plurality of candidate viewpoints;
- generate the at least one volume-viewing image from the three-dimensional image data with respect to the selected viewpoint; and
- display the generated at least one volume-viewing image including the region of the visible surface with respect to the selected viewpoint, wherein individual transfer functions are separately assigned to the segmented functional structures.

16. The system of claim 15, wherein each of the plurality of different viewing spheres is associated with a different view-relevant parameter.

* * * * *